United States Patent [19]

Odenwälder et al.

[11] Patent Number: 5,035,987
[45] Date of Patent: Jul. 30, 1991

[54] COLOR PHOTOGRAPHIC RECORDING MATERIAL CONTAINING A DIR COUPLER

[75] Inventors: Heinrich Odenwälder; Thomas Krüger, both of Leverkusen; Hans-Joachim Schumann, Cologne, all of Fed. Rep. of Germany

[73] Assignee: Agfa Gevaert Aktiengesellschaft, Leverkusen, Fed. Rep. of Germany

[21] Appl. No.: 586,516

[22] Filed: Sep. 21, 1990

[30] Foreign Application Priority Data

Oct. 5, 1989 [DE] Fed. Rep. of Germany ....... 3933238

[51] Int. Cl.$^5$ .............................................. G03C 7/36
[52] U.S. Cl. .................................. 430/544; 430/556; 430/557; 430/558
[58] Field of Search ........... 430/556, 557, 554, 558 R, 430/558 A

[56] References Cited

U.S. PATENT DOCUMENTS

| 2,154,918 | 4/1939 | Schneider et al. | 430/556 |
| 2,312,040 | 2/1943 | Kendall et al. | 430/556 |
| 3,277,554 | 1/1966 | Barr et al. | 430/544 |
| 4,801,520 | 1/1989 | Inoue et al. | 430/544 |

Primary Examiner—Richard L. Schilling
Attorney, Agent, or Firm—Connolly & Hutz

[57] ABSTRACT

Where DIR couplers corresponding to formula I are used in color photographic silver halide materials, good edge effects and interimage effects are obtained.

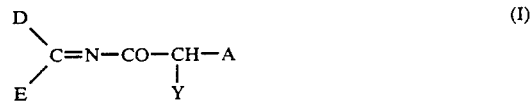

(I)

In formula (I),

A represents halogen, —OR, —SR, —CN, —COR, —CONHR, —COOR, —SO$_2$R, —SO$_2$NHR,

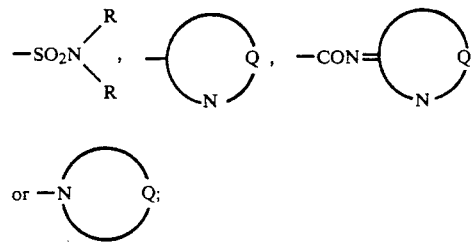

R represents alkyl, aralkyl, aryl or hetaryl;
Q represents a substituent for compelting a 5- or 6-membered heterocyclic ring;
D and E, which may be the same or different, represent substituents attached to the C atom of the C=N group by a C, O, S or N atom, including those substituents which, together with the C atom of the C=N group, complete a carbocyclic or heterocyclic ring;
Y represents a group having a silver halide development inhibiting function which is releasable during color development.

2 Claims, No Drawings

COLOR PHOTOGRAPHIC RECORDING MATERIAL CONTAINING A DIR COUPLER

This invention relates to a color photographic recording material comprising at least one photosensitive silver halide emulsion layer containing a coupler which releases a development inhibitor during color development.

It is known that chromogenic development can be carried out in the presence of compounds which, during development, release substances that are capable of exerting certain effects, for example influencing the development of silver halide. If this effect is that further development is inhibited, compounds of the type in question are called DIR (development inhibitor releasing) compounds. The DIR compounds may be of the type which react with the oxidation product of a color developer to form a dye with elimination of an inhibitor group (DIR couplers) or of the type which release the inhibitor without at the same time forming a dye. Compounds of the latter type are also called DIR compounds in a narrower sense.

DIR couplers are known, for example, from U.S. Pat. No. 3,148,602, U.S. Pat. No. 3,227,554, U.S. Pat. No. 3,615,506, U.S. Pat. No. 3,617,291 and DEAA-24 14 006.

The development inhibitors released are generally heterocyclic mercapto compounds or derivatives of benzotriazole. DIR couplers which release monocyclic triazoles as development inhibitor are described, for example, in DE-A-28 42 063 and in DE-A-0 272 573. A number of photographic effects influencing image quality can be obtained by using DIR compounds. Such effects include, for example, the reduction of gradation, the formation of a finer color grain, the improvement of definition by the so-called edge effect and the improvement of color purity and color brilliance by so-called interimage effects, cf. for example the Article entitled "Development-Inhibitor-Releasing (DIR) Couplers in Color Photography" by C. R. Barr, J. R. Thirtle and P. W. Vittum in Photographic Science and Engineering 13, 74 (1969).

DIR compounds which couple without dye formation have the advantage over DIR couplers which couple with dye formation that they can be universally used so that the same compound may be used in all photosensitive layers of a color photographic recording material irrespective of the color to be produced. By contrast, on account of the color produced from them, DIR couplers can generally only be used in some of the photosensitive layers unless the secondary color density attributable to them can be tolerated in the other layers. This advantage of DIR compounds is offset by the disadvantage that they are generally less reactive than DIR couplers. In practice, therefore, DIR couplers only are used, two or more different DIR couplers being used where necessary in the same recording material. Different DIR couplers may be associated with the differently spectrally sensitized layers according to the color produced from them.

It is normally important that the development inhibitor be rapidly released from the coupler during development because it is intended to influence the further course of the development process. Accordingly, it is highly desirable that the couplers in question show high activity. Highly active DIR couplers are described, for example, in EP-A-0 287 833.

A further demand on DIR couplers concerns their stability under storage in a wide range of practical conditions, as temperature and humidity.

Under forced conditions of storage, still in the range of practical use for photographic materials, for instance photographic films, DIR couplers of the prior art often are damaged with the effect that they loose their activity or that they release the inhibitor moiety in an uncontrolled way. This would result in highly undesired effects, i.e. diminishing of color reproduction, tonal reproduction and/or sensitivity.

Therefore, it was desired that DIR couplers strongly resist to these storage conditions.

The problem addressed by the present invention is to provide a color photographic recording material containing a DIR coupler with a silver halide development inhibitor attached to the coupling position from which the inhibitor is rapidly released during development.

The present invention relates to a color photographic recording material comprising at least one photosensitive silver halide emulsion layer and a DIR coupler associated therewith, characterized in that the coupler corresponds to formula I $$\begin{array}{c} D \\ \phantom{x} \diagdown \\ \phantom{xxx} C=N-CO-CH-A \\ \phantom{x} \diagup \phantom{xxxxxxxxxx} | \\ E \phantom{xxxxxxxxxxx} Y \end{array} \quad (I)$$

in which
A represents halogen, —OR, —SR, —CN, —COR, —CONHR, —COOR, —SO₂R, —SO₂NHR,

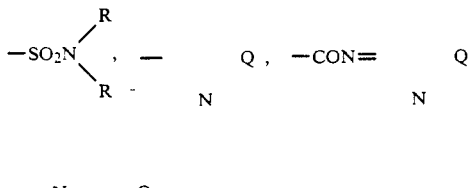

R represents alkyl, aralkyl, aryl or hetaryl;
Q represents a substituent for completing a 5- or 6-membered heterocyclic ring;
D and E, which may be the same or different, represent substituents attached to the C atom of the C=N group by a C, O, S or N atom, including those substituents which, together with the C atom of the C=N group, complete a carbocyclic or heterocyclic ring;
Y is a group which is releasable during development and which, optionally after elimination of a part of this group, has a certain photographic activity, more particularly a group having a silver halide development inhibiting function.

A substituent R mentioned in formula I for A may be alkyl, aralkyl or aryl. Alkyl is linear or branched and contains up to 18 carbon atoms; aralkyl is, for example, benzyl and aryl is, for example, phenyl. The alkyl, aralkyl and aryl radicals may optionally be further substituted, for example by halogen, —CF₃, —CN, alkyl, alkoxy, acylamino, carbamoyl, alkoxycarbonyl, sulfamoyl. Two substituents R together with an N atom to which they are attached may complete a cyclic amino group, for example pyrrolidino, piperidino, morpholino.

The following are examples of heterocyclic rings completed by Q:

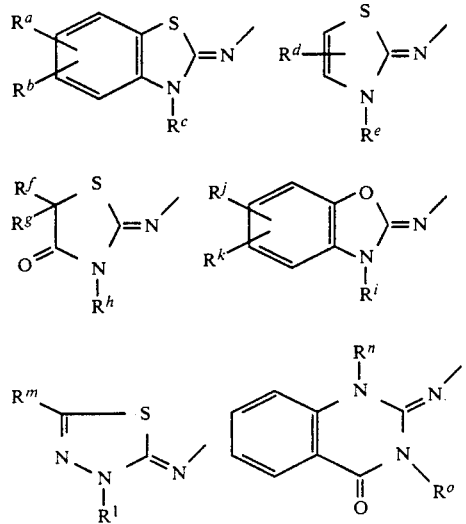

The substituents $R^a$ to $R^q$ are substituents of the type which may be represented in typical syntheses of these heterocyclic rings, for example alkyl, aryl, hetaryl, halogen, alkoxy, acyl groups, nitro and sulfamoyl.

The substituents $R^c$, $R^e$, $R^h$, $R^i$, $R^l$, $R^n$ and $R^o$ are generally such radicals as, for example, alkyl, aryl.

The substituents represented by D and E are, in particular, substituents attached by an S atom to the C atom of the C=N group, for example alkylthio, aralkylthio or arylthio. Heterocyclic rings completed by D and E are, for example, the rings of benzoxazole, benzthiazole, quinazolone, thiazolidone.

The photographically active substituent represented by Y in formula I is, in particular, a substituent having a silver halide development inhibiting function and corresponds to the following formula:

$$-(TIME)_n-INH$$

where INH is a silver halide development inhibitor, n=0 or 1 and the binding link represented by TIME is a group which, after release from the coupling position of the coupler during its coupling with the oxidation product of the silver halide developer, is capable of releasing the inhibitor attached thereto in a following reaction. The group TIME is also called a timing group because, where a group such as this is present, the inhibitor attached thereto is in many cases released and can become active with delay. Known timing groups include, for example, the group

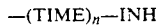

where the O atom is attached to the coupling position of the coupler while the C atom is attached to an N atom of an inhibitor (for example DE-A-27 03 145), a group which undergoes an intramolecular nucleophilic displacement reaction after release from the coupler and, in the process, releases the inhibitor (for example DE-A-28 55 697), a group in which, after release from the coupler, an electron transfer can take place along a conjugated system, resulting in release of the inhibitor (for example DE-A-31 05 026) or the group

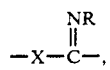

where X (for example —O—) is attached to the coupling position of the coupler and the C atom is attached to an atom of the inhibitor and in which R represents aryl for example (for example EP-A-0 127 063).

TIME may also be a group RED which, after elimination from the coupler, can enter into a redox reaction with the oxidation product of the developer and, as a result, releases the group INH (for example EP-A-0 204 175).

The group TIME may be present or even completely absent (where n=0).

The releasable group represented by Y is, for example, an organic group generally attached to the coupling position of the coupler molecule by a sulfur or nitrogen atom (optionally via a group TIME). If the releasable group is a cyclic group, it may be attached to the coupling position of the coupler molecule (or to the group TIME) either directly via an atom which is part of a ring, for example a nitrogen atom, or indirectly via an intermediate binding link. Releasable groups such as these are known in large numbers.

The rings in question are all 5- or 6-membered heterocyclic rings which are attached by a ring nitrogen atom or by a sulfur atom to the coupling position of the coupler or the group TIME. The heterocyclic rings often contain activating groups, for example carbonyl or sulfonyl groups or double bonds, adjacent the nitrogen atom establishing the link to the coupler molecule.

If the releasable group is attached to the coupling position of the coupler by a sulfur atom, it may be the residue of a diffusible mercapto compound which is capable of inhibiting the development of silver halide. Inhibitor groups such as these have often been described as releasable groups attached to the coupling position of couplers, including open-chain ketomethylene couplers, for example in U.S. Pat. No. 3,227,554.

The releasable group is, for example, the residue of a photographically active compound containing a 5-membered heterocyclic ring which is attached to the coupling position of the coupler or to TIME by a sulfur atom (example: tetrazolylthio, oxadiazolylthio, thiadiazolylthio), or the residue of a photographically active compound attached to the coupling position of the coupler or to the timing group TIME by a nitrogen atom of a 1,2,3- or 1,2,4-triazole ring, the 1,2,3-triazole ring optionally containing a fused benzene ring.

In one preferred embodiment, the DIR coupler corresponds to general formula II

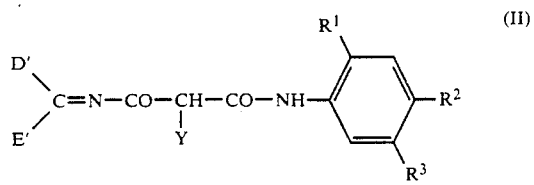

in which

D' and E' together represent a substituent for completing a heterocyclic ring to which a benzene ring may be fused, R$^1$ is hydrogen, halogen, alkoxy or aroxy;
R$^2$ is hydrogen, alkoxy, alkoxycarbonyl;
R$^3$ is hydrogen, sulfamoyl, N-alkyl sulfamoyl, N-acyl sulfamoyl, alkoxycarbonyl, acylamino;
Y is a substituent having a silver halide development inhibiting function which is releasable during the color coupling reaction.

The following are examples of DIR couplers according to the invention:

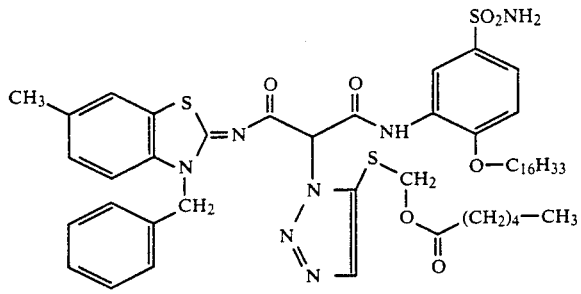

DIR-1

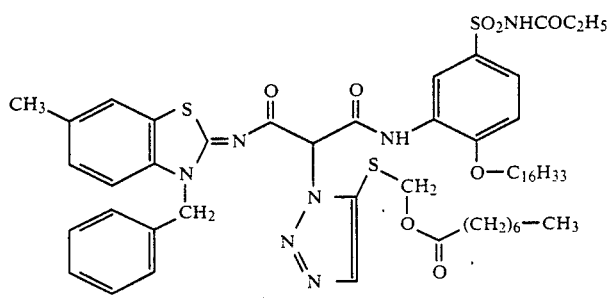

DIR-2

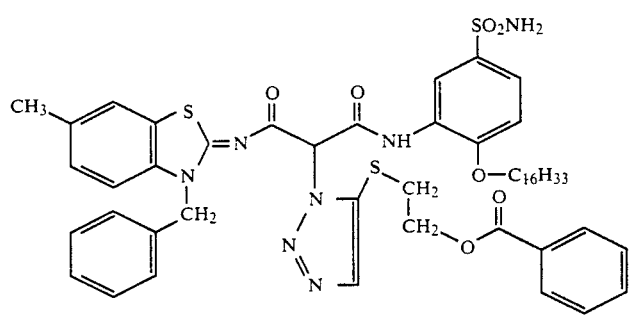

DIR-3

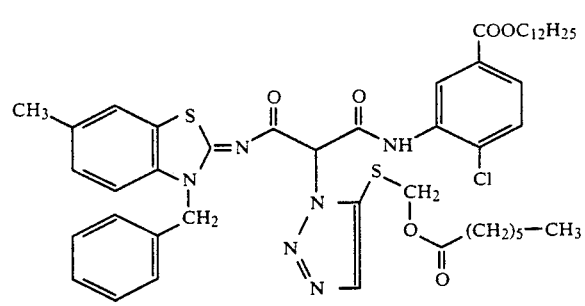

DIR-4

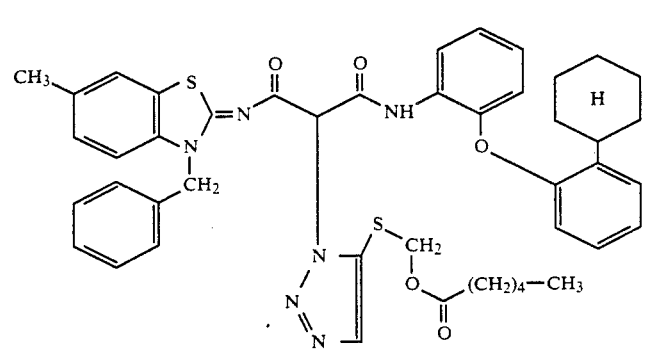

DIR-5

-continued
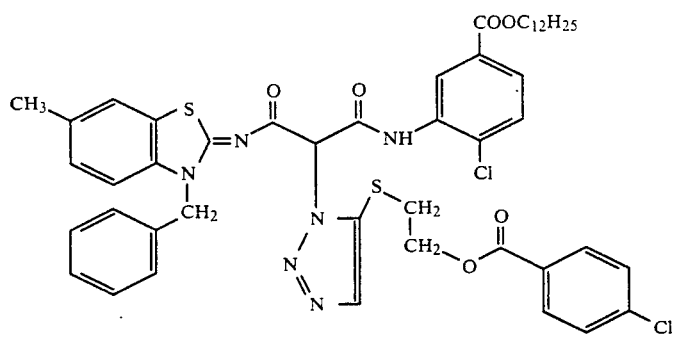
DIR-6
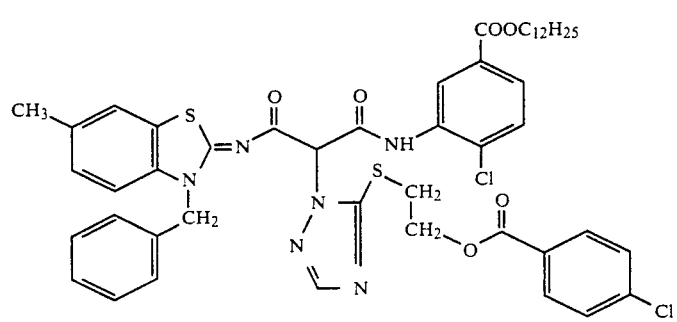
DIR-7
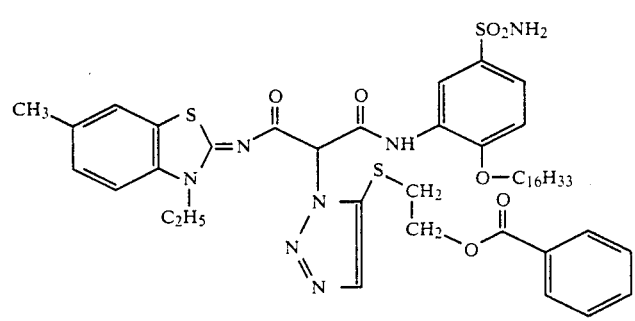
DIR-8
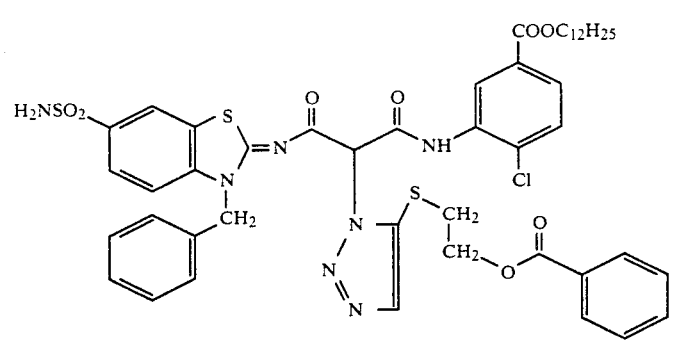
DIR-9
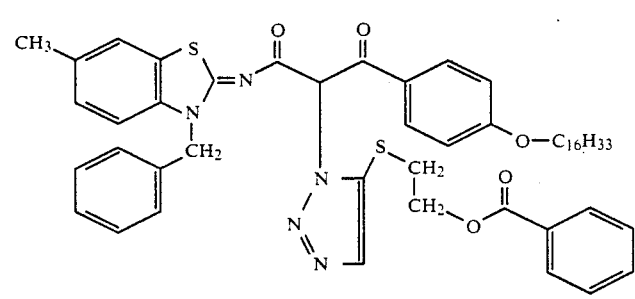
DIR-10

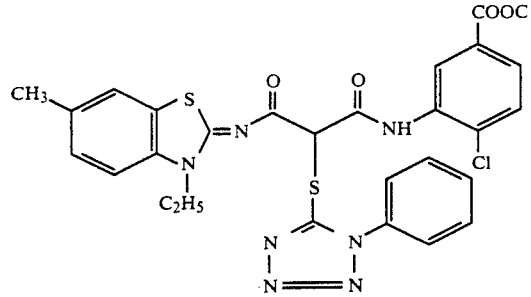
DIR-11
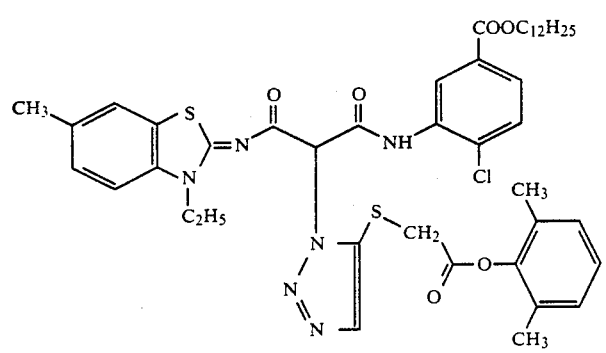
DIR-12
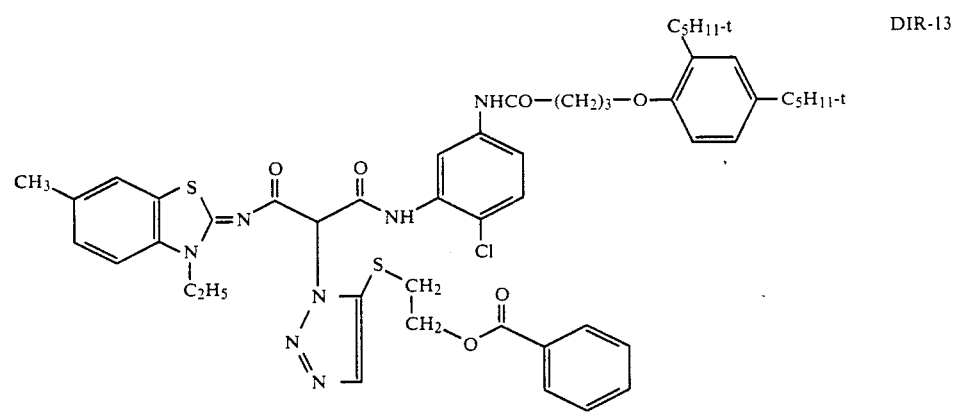
DIR-13
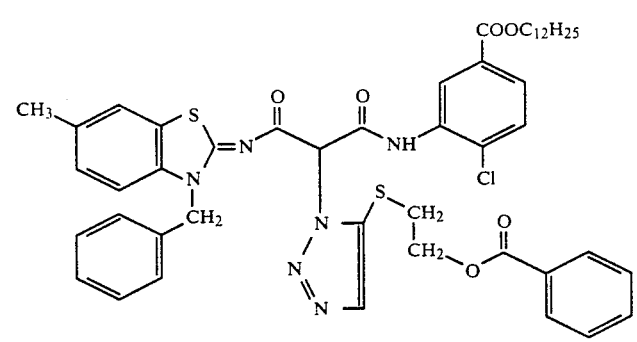
DIR-14
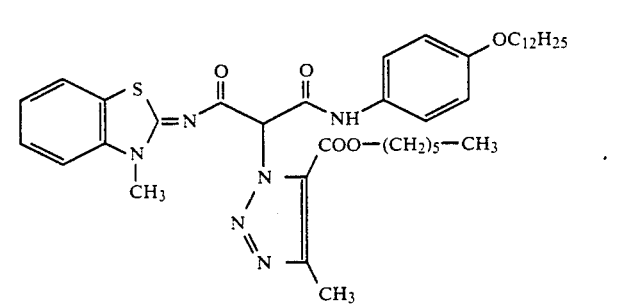
DIR-15

-continued
DIR-16
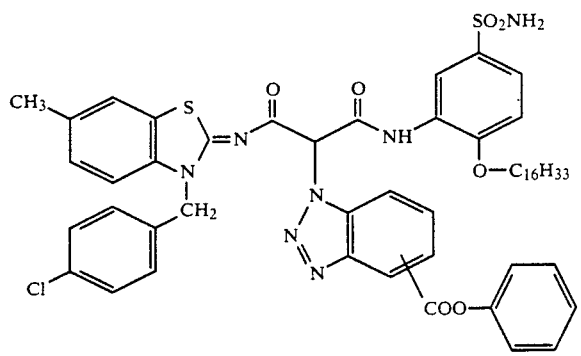
DIR-17
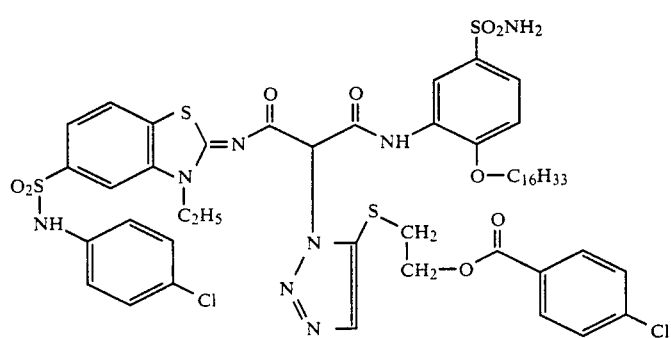
DIR-18
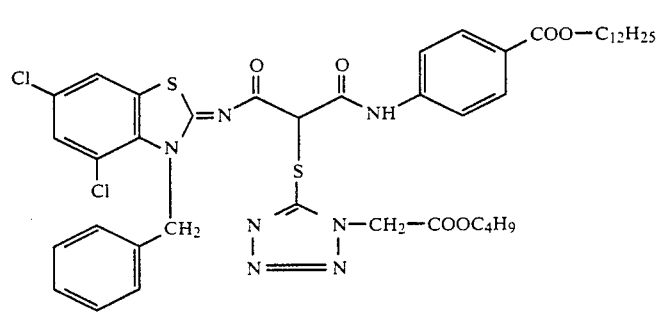
DIR-19
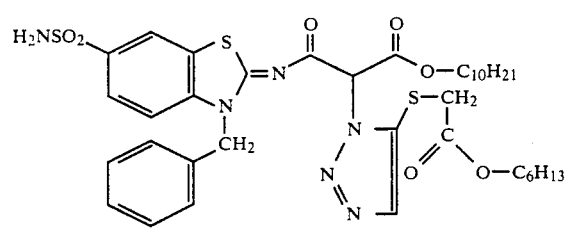
DIR-20
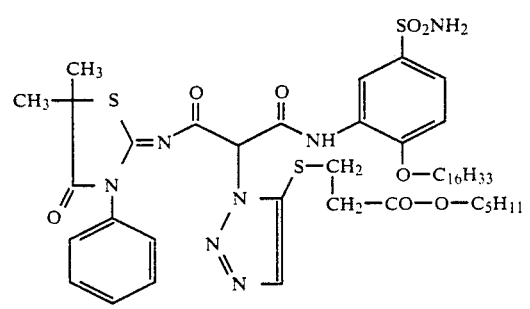

-continued
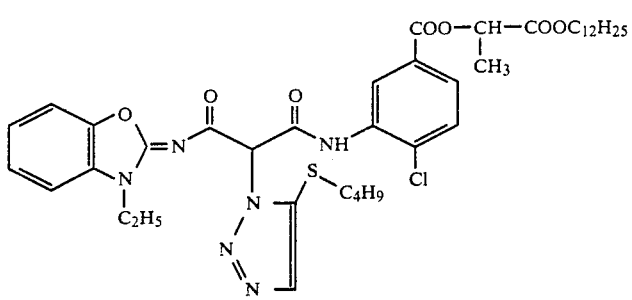
DIR-21
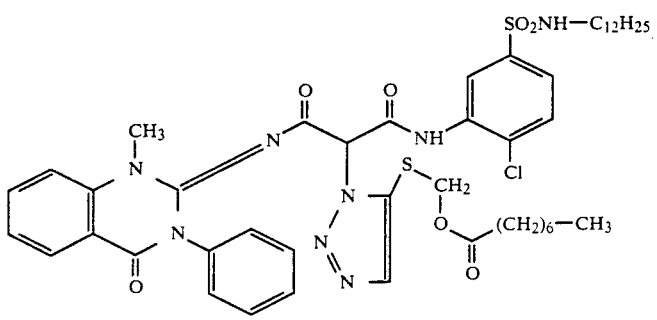
DIR-22
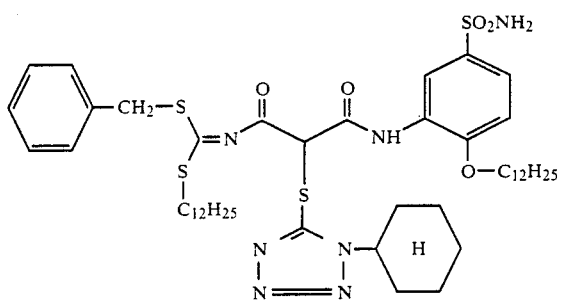
DIR-23
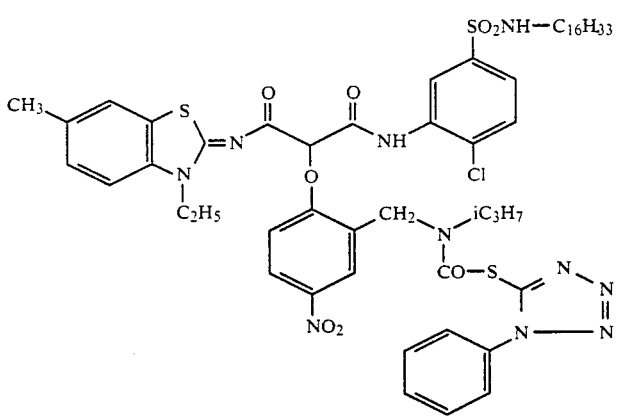
DIR-24
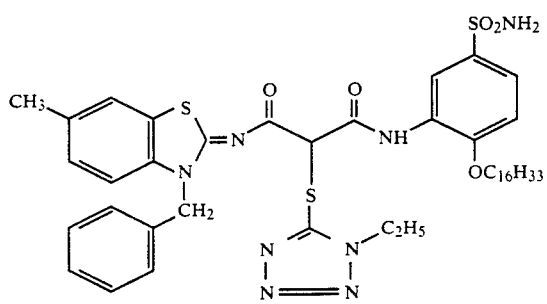
DIR-25

-continued
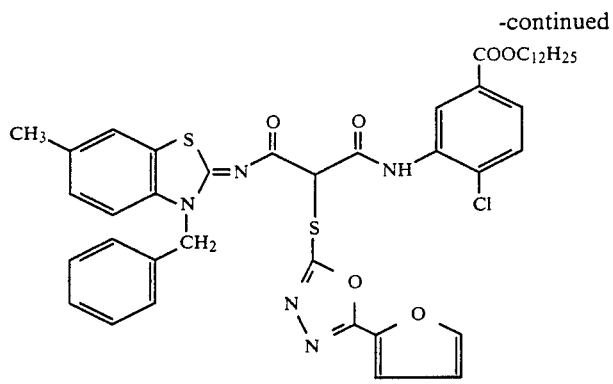
DIR-26
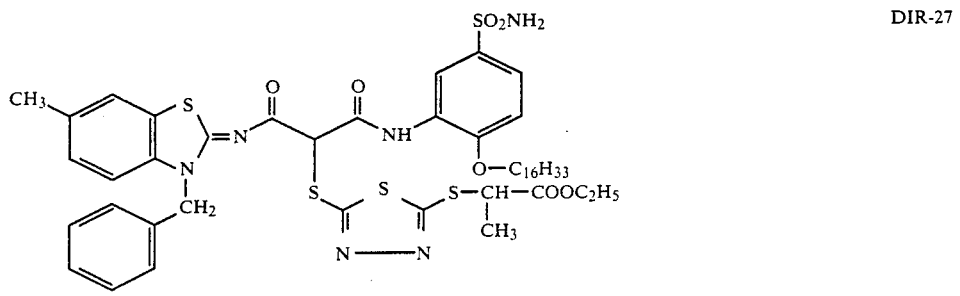
DIR-27
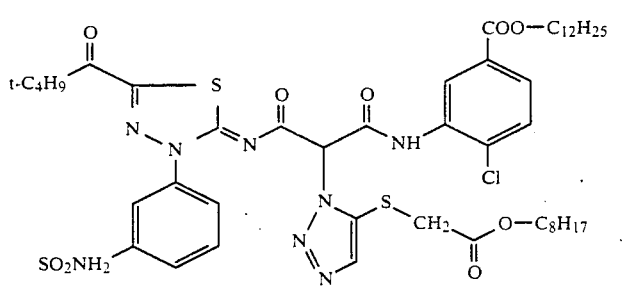
DIR-28
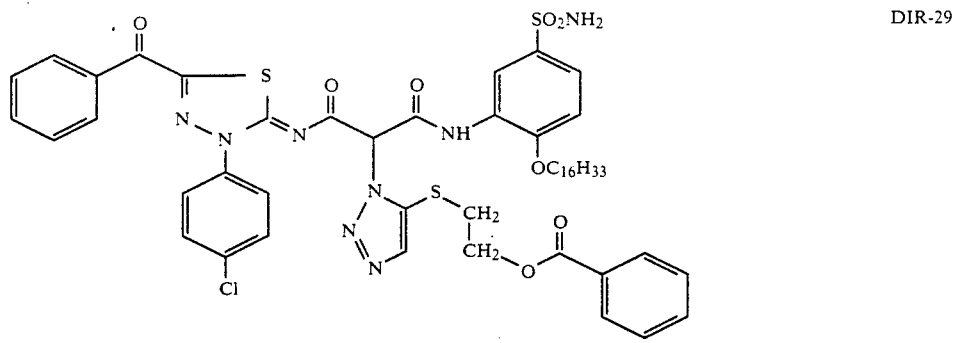
DIR-29
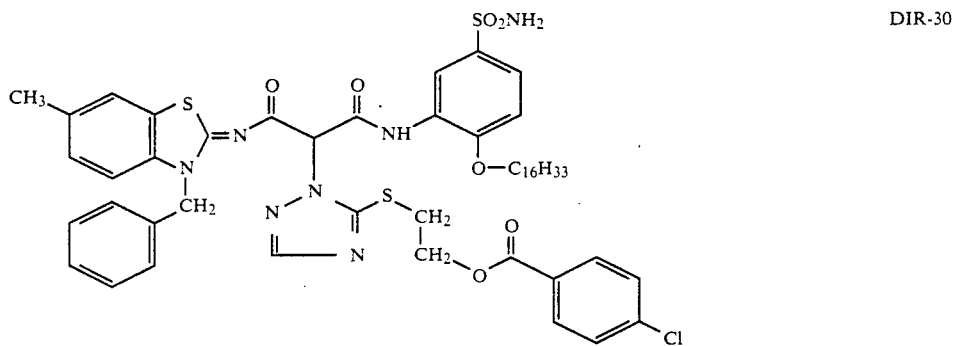
DIR-30

DIR-31

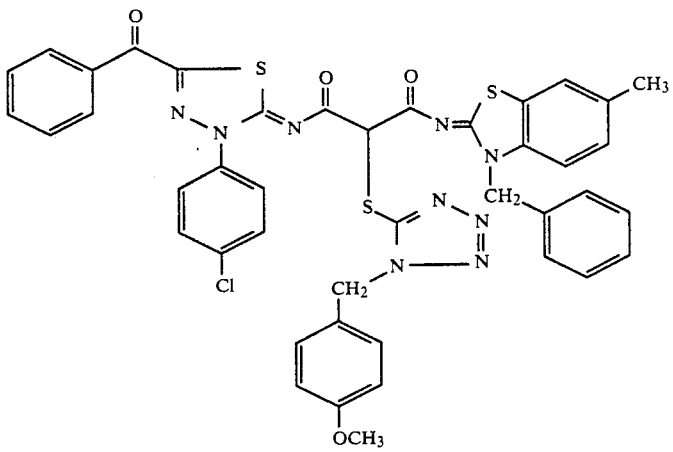

DIR-32

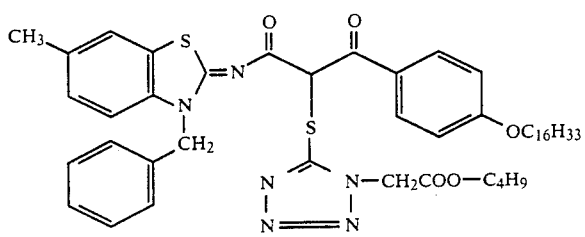

DIR-33

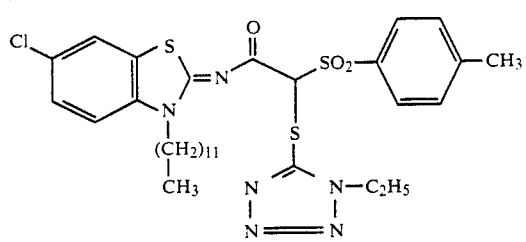

DIR-34

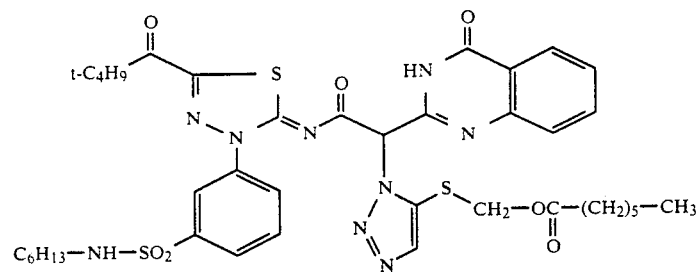

Preparation of DIR coupler DIR-1

A) 4-(n-pentylcarbonyloxymethylthio)-1,2,3-triazole 23.1 g hexanoic acid chloromethyl ester are added over a period of 30 minutes with stirring to 17.2 g 4-mercapto-1,2,3-triazole, sodium salt, in 100 ml dimethyl formamide. After 2 h, the mixture is added to 600 ml ice water and the oil formed is taken up in ethyl acetate.

The organic phase is separated off, washed successively with dilute NaHCO₃ solution, 2 N HCl and water and then dried over Na₂SO₄. 22 g of the crude product A in the form of an oil are obtained after removal of the solvent. 13.2 g of compound A in crystalline form are obtained therefrom by the addition with cooling of 200 ml petroleum ether.

B) 3-Benzyl-6-methyl benzthiazolone imine 5.15 ml bromine in 25 ml glacial acetic acid are added dropwise over a period of 45 minutes with stirring at 15° to 20° C. to 23.4 g N-benzyl-4-toluidine hydrochloride and 19.4 g potassium thiocyanate in 200 ml glacial acetic acid.

After another 30 minutes, the precipitate is filtered off under suction and washed with glacial acetic acid and then with ice water and acetonitrile.

The free imino compound B is obtained from a precipitate with a slight excess of NaOH. Yield: 14.5 g.

α-Ethoxycarbonyl-2-hexadecyloxy-5-sulfamoyl acetanilide 39 ml methane sulfonic acid are added with stirring to 238 g 3-amino-4-cetyloxy benzene sulfonamide and 102 g malonic acid monoethyl ester, potassium salt, in 2,500 ml ethyl acetate. 174 g N,N'-dicyclohexyl carbodiimide are then added and, after another 2 h, the reaction mixture is heated to 60° C. After the precipitate has been filtered off under suction, the filtrate is concentrated in a rotary evaporator and the residue obtained is stirred with 1,500 ml methanol. The precipitate is separated off and then washed with 500 ml methanol. Yield: 227 g.

D) α-(3-Benzyl-6-methyl benzthiazoloneiminocarbonyl)-2'-hexadecyloxy-5'-sulfamoyl acetanilide 101.8 g of compound B and 210.7 g of compound C are mixed and heated with stirring to 170° to 180° C. After 1 h, the mixture is left to cool to 150° C. 600 ml dimethyl acetamide are slowly added to the reaction mixture. The solution obtained is cooled to 30° C., followed by the addition of 2,000 ml methanol. After cooling to 10° C., the precipitate obtained is separated off and washed with 1,000 ml methanol. Yield: 244 g.

E) Bromination of D 2.04 ml bromine are added to 29 g of compound D in 250 ml glacial acetic acid at 50° to 60° C. After 15 minutes, the mixture is cooled to room temperature and 200 ml methanol are added. The precipitate formed is separated off and washed with methanol. Yield: 24 g.

Compound DIR-1

40.7 g of compound E and 11.46 g of compound A are successively dissolved in 300 ml dimethyl acetamide and 13 ml tetramethyl guanidine are added to the resulting solution. After stirring for 1.5 h at room temperature, the mixture is poured onto ice water to which glacial acetic acid has been added for neutralization.

The precipitate formed is filtered under suction and successively washed with water and methanol.

The crude product obtained (38.7 g) is recrystallized from 800 ml of a mixture of methanol and ethyl acetate (ratio 8:2) with the aid of charcoal. Yield: 22.3 g.

Excellent interimage and edge effects are obtained with the DIR couplers according to the invention and lead to excellent color reproduction and detail reproduction. In contrast to standard DIR couplers of the acyl acetanilide type, they show high stability in storage under humid and/or hot conditions. Preferred DIR couplers are those of which the inhibitor, after elimination from the coupler and diffusion in the developer solution, is decomposed after a short time to products having no further photographic activity.

Most useful DIR couplers exhibit $pK_a$ values between 10.5 and 7.0, as determined in dimethyl sulfoxide with tetrabutyl ammonium hydroxide. For special effects, e.g. when it is desired mainly to influence grannularity of the photographic material, $pK_4$ values outside these limits also may be acceptable.

The high activity of the DIR couplers according to the invention is reflected in the fact that, during development, they release the development inhibitor in sufficient quantities and at a sufficient rate.

It is clear that these properties are also expected from couplers which are intended to eliminate another photographically active group, for example a development-accelerating or fogging group, both of which can also only be activated by development. Accordingly, the group can consist not only in a development inhibitor group, but also in an another photographically active group.

Couplers containing hetarylidene imino groups were already known, cf. for example U.S. Pat. No. 2,312,040 and Bull Soc. Chem. Belg. 61 (1952), pages 245-252.

These couplers are 4-equivalent couplers and, hitherto, have evidently not been used in photographic materials.

There is nothing in either publication to suggest that these partial coupler structures would be suitable as 2-equivalent couplers for eliminating photographically active groups.

The compounds according to the invention are suitable for use as DIR couplers in color photographic, more especially multilayer, recording materials. Where they are yellow couplers, they are preferably used in, or in association with, a photosensitive silver halide emulsion layer predominantly sensitive to the blue spectral region of visible light. The particular advantage of the couplers according to the invention, namely the comparatively low inhibition of development in the layer with which such a compound is associated in addition to the comparatively high inhibition of development in adjacent, non-associated layers, is of course particularly relevant in the case of a multilayer color photographic recording material which, in addition to a predominantly blue-sensitive silver halide emulsion layer, contains other photosensitive silver halide emulsion layers predominantly sensitive to the green or red spectral region of visible light.

By virtue of their extremely high activity, the DIR couplers according to the invention may also be used in comparatively small quantities as color couplers to produce the desired effects, particularly the inter-image effects. For example, this enables a yellow DIR coupler according to the invention to be used not only in the blue-sensitive layers producing yellow dye, but also in other layers without an excessive, unwanted secondary density occurring in those layers. Accordingly, the DIR couplers according to the invention may also be advantageously used as yellow couplers in magenta layers and in cyan layers.

In the production of the photosensitive photographic recording material, the non-diffusing DIR couplers according to the invention may be incorporated in the casting solution of the silver halide emulsion layers or other colloid layers in known manner, optionally together with other couplers. For example, oil-soluble or hydrophobic couplers may be added to a hydrophilic colloid solution, preferably from a solution in a suitable coupler solvent (oil former), optionally in the presence of a wetting agent or dispersant. In addition to the binder, the hydrophilic casting solution may of course contain other typical additives. The solution of the coupler need not be directly dispersed in the casting solution for the silver halide emulsion layer or any other water-permeable layer; instead, it may advantageously first be dispersed in an aqueous nonphotosensitive solution of a hydrophilic colloid and the mixture obtained, optionally after removal of the low-boiling organic solvent used, may be mixed with the casting solution for the photosensitive silver halide emulsion layer or any other water-permeable layer before application.

Suitable photosensitive silver halide emulsions are emulsions of silver chloride, silver bromide or mixtures thereof, optionally with a small content of silver iodide of up to 20 mol-%, in one of the hydrophilic binders typically used. Gelatine is preferably used as binder for the photographic layers, although it may be completely or partly replaced by other natural or synthetic binders.

The emulsions may be chemically and spectrally sensitized in the usual way and the emulsion layers and other non-photosensitive layers may be hardened in the usual way with known hardeners.

Color photographic recording materials typically contain at least one silver halide emulsion layer for recording light of each of the three spectral regions red, green and blue. To this end, the photosensitive layers are spectrally sensitized in known manner by suitable sensitizing dyes. Blue-sensitive silver halide emulsion layers do not necessarily have to contain a spectral sensitizer because, in many cases, the natural sensitivity of the silver halide is sufficient for recording blue light.

Each of the photosensitive layers mentioned may consist of a single layer or, in known manner, for example as in the so-called double layer arrangement, may also comprise two or even more partial silver halide emulsion layers (DE-C-1 121 470). Normally, red-sensitive silver halide emulsion layers are arranged nearer the layer support than green-sensitive silver halide emulsion layers which in turn are arranged nearer than blue-sensitive emulsion layers, a non-photosensitive yellow filter layer generally being arranged between the green-sensitive layers and blue-sensitive layers. However, other arrangements are also possible. A non-photosensitive intermediate layer, which may contain agents to prevent the unwanted diffusion of developer oxidation products, is generally arranged between layers of different spectral sensitivity. Where several silver halide emulsion layers of the same spectral sensitivity are present, they may be arranged immediately adjacent one another or in such a way that a photosensitive layer of different spectral sensitivity is present between them (DE-A-1 958 709, DE-A-25 30 645, DE-A-26 22 922).

Color photographic recording materials for the production of multicolor images normally contain dye-producing compounds, in the present case particularly color couplers, for producing the cyan, magenta and yellow dye images in spatial and spectral association with the silver halide emulsion layers of different spectral sensitivity.

In the context of the invention, spatial association means that the color coupler is present in such a spatial relationship to the silver halide emulsion layer that the two are capable of interacting in such a way as to allow imagewise accordance between the silver image formed during development and the dye image produced from the color coupler. This result is generally achieved by the fact that the color coupler is contained in the silver halide emulsion layer itself or in an adjacent, optionally nonphotosensitive binder layer.

By spectral association is meant that the spectral sensitivity of each of the photosensitive silver halide emulsion layers and the color of the component dye image produced from the particular spatially associated color coupler bear a certain relationship to one another, a component dye image relating to another color (for example cyan magenta or yellow) being associated with each of the spectral sensitivities (red, green, blue).

One or more color couplers may be associated with each of the differently spectrally sensitized silver halide emulsion layers. Where several silver halide emulsion layers of the same spectral sensitivity are present, each of them may contain a color coupler, the color couplers in question not necessarily having to be the same. They are merely required to produce at least substantially the same color during color development, normally a color which is complementary to the color of the light to which the silver halide emulsion layers in question are predominantly sensitive.

In preferred embodiments, at least one non-diffusing color coupler for producing the cyan component dye image is associated with red-sensitive silver halide emulsion layers, at least one non-diffusing color coupler for producing the magenta component dye image is associated with green-sensitive silver halide emulsion layers and at least one non-diffusing color coupler for producing the yellow component dye image is associated with blue-sensitive silver halide emulsion layers.

However, other associations are also possible.

Color couplers for producing the cyan dye image are generally couplers of the phenol or α-naphthol type, of which suitable examples are:

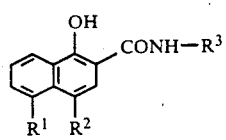

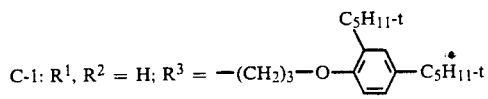
C-1: $R^1, R^2 = H; R^3 = -(CH_2)_3-O-\langle\text{aryl}\rangle-C_5H_{11}\text{-t}$

C-2: $R^1 = -NHCOOCH_2-CH(CH_3)_2; R^2 = H;$
$R^3 = -(CH_2)_3-OC_{12}H_{25}$

C-3: $R^1 = H; R^2 = -OCH_2-CH_2-SO_2CH_3; R^3 = -C_{16}H_{33}$

C-4: $R^1 = H; R^2 = -OCH_2-CONH-(CH_2)_2-OCH_3;$
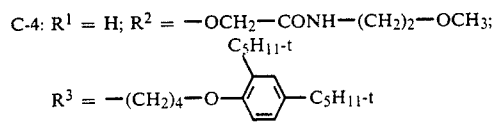
$R^3 = -(CH_2)_4-O-\langle\text{aryl}\rangle-C_5H_{11}\text{-t}$

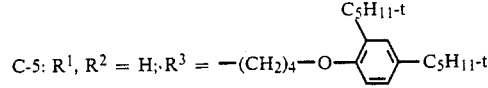
C-5: $R^1, R^2 = H; R^3 = -(CH_2)_4-O-\langle\text{aryl}\rangle-C_5H_{11}\text{-t}$

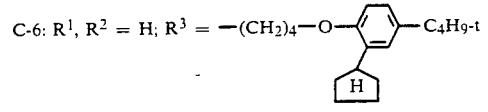
C-6: $R^1, R^2 = H; R^3 = -(CH_2)_4-O-\langle\text{aryl}\rangle-C_4H_9\text{-t}$ C-7: $R^1 = H; R^2 = Cl; R^3 = -C(C_2H_5)_2-C_{21}H_{43}$ C-8: $R^1 = H; R^2 = -O-CH_2-CH_2-S-CH(COOH)-C_{12}H_{25}$
$R^3 = $ Cyclohexyl

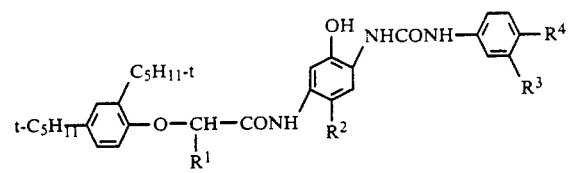

C-9: $R^1 = -C_4H_9; R^2 = H; R^3 = -CN; R^4 = Cl$

C-10: $R^1 = -C_4H_9; R^2 = H; R^3 = H; R^4 = -SO_2CHF_2$

C-11: $R^1 = -C_4H_9;$
$R^2 = -O-\langle\text{aryl}\rangle-C(CH_3)_2-CH_2-C(CH_3)_3;$
$R^3 = H; R^4 = -CN$

C-12: $R^1 = C_2H_5; R^2, R^3 = H; R^4 = -SO_2CH_3$

C-13: $R^1 = -C_4H_9; R^2, R^3 = H; R^4 = -SO_2-C_4H_9$

C-14: $R^1 = -C_4H_9; R^2 = H; R^3 = -CN; R^4 = -CN$

C-15: $R^1 = -C_4H_9; R^2, R^3 = H; R^4 = -SO_2-CH_2-CHF_2$

C-16: $R^1 = -C_2H_5; R^2, R^3 = H;$
$R^4 = -SO_2CH_2-CHF-C_3H_7$

C-17: $R^1 = -C_4H_9$; $R^2, R^3 = H$; $R^4 = F$

C-18: $R^1 = -C_4H_9$; $R^2, R^3 = H$; $R^4 = -SO_2CH_3$

C-19: $R^1 = -C_4H_9$; $R^2, R^3 = H$; $R^4 = -CN$

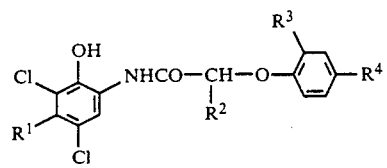

C-20: $R^1 = -CH_3$; $R^2 = -C_2H_5$; $R^3, R^4 = -C_5H_{11}$-t

C-21: $R^1 = -CH_3$; $R^2 = H$; $R^3, R^4 = -C_5H_{11}$-t

C-22: $R^1, R^2 = -C_2H_5$; $R^3, R^4 = -C_5H_{11}$-t

C-23: $R^1 = -C_2H_5$; $R^2 = -C_4H_9$; $R^3, R^4 = -C_5H_{11}$-t

C-24: $R^1 = -C_2H_5$; $R^2 = -C_4H_9$; $R^3, R^4 = -C_4H_9$-t

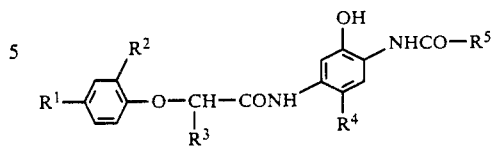

C-25: $R^1, R^2 = -C_5H_{11}$-t; $R^3 = -C_4H_9$; $R^4 = H$; $R^5 = -C_3F_7$

C-26: $R^1 = -NHSO_2-C_4H_9$; $R^2 = H$; $R^3 = -C_{12}H_{25}$; $R^4 = Cl$; $R^5 = $ Phenyl C-27: $R^1, R^2 = -C_5H_{11}$-t; $R^2 = Cl$, $R^3 = -C_3H_7$-i; $R^4 = Cl$; $R^5 = $ pentaflourophenyl C-28: $R^1 = -C_5H_{11}$-t; $R^2 = Cl$; $R^3 = -C_6H_{13}$; $R^4 = Cl$; $R^5 = $ -2-chlorophenyl Color couplers for producing the magenta dye image are generally couplers of the 5-pyrazolone, inadazolone or pyrazoloazole type, of which suitable examples are:

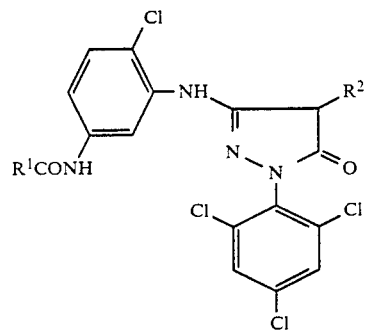

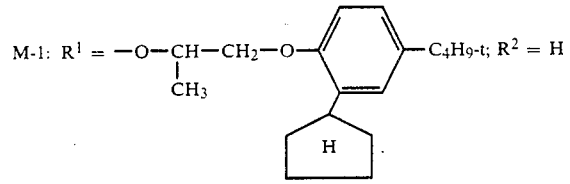

M-1: $R^1 = -O-\underset{\underset{CH_3}{|}}{CH}-CH_2-O-\phantom{X}-C_4H_9$-t; $R^2 = H$

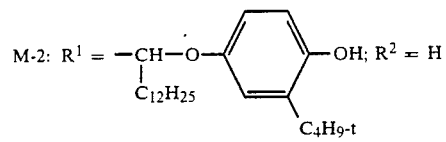

M-2: $R^1 = -\underset{\underset{C_{12}H_{25}}{|}}{CH}-O-\phantom{X}-OH$; $R^2 = H$, $C_4H_9$-t

M-3: $R^1 = -C_{13}H_{27}$; $R^2 = H$

M-4: $R^1 = -OC_{16}H_{33}$; $R^2 = H$

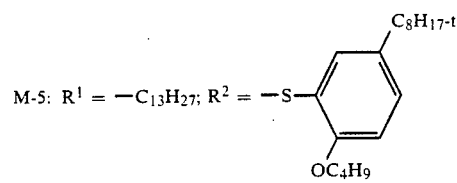

M-5: $R^1 = -C_{13}H_{27}$; $R^2 = -S-$

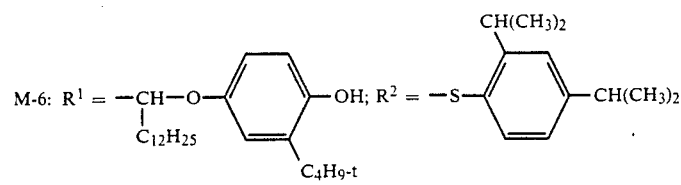

M-6: $R^1 = -\underset{\underset{C_{12}H_{25}}{|}}{CH}-O-$ ; $R^2 = -S-$

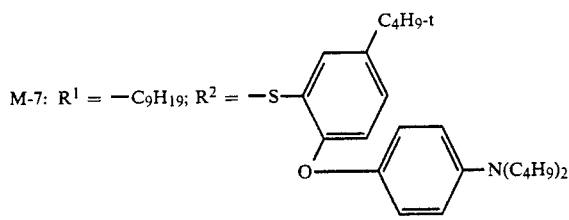
M-7: $R^1 = -C_9H_{19}$; $R^2 = $ (structure shown)
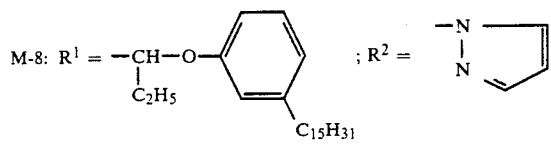
M-8: $R^1 = $ (structure shown); $R^2 = $ (structure shown)
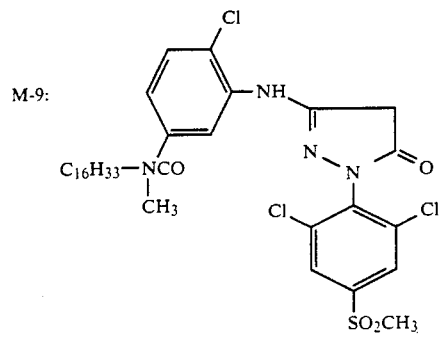
M-9:
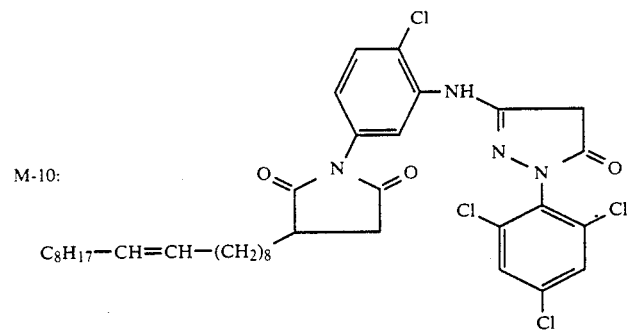
M-10:
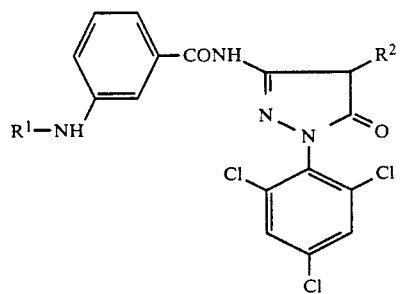
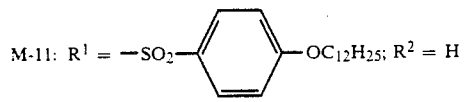
M-11: $R^1 = -SO_2$—⟨phenyl⟩—$OC_{12}H_{25}$; $R^2 = H$
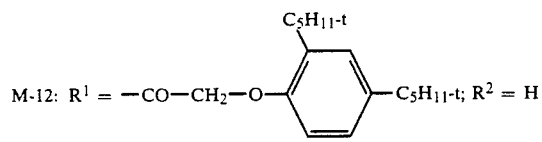
M-12: $R^1 = -CO-CH_2-O$—⟨phenyl with $C_5H_{11}$-t substituents⟩—$C_5H_{11}$-t; $R^2 = H$

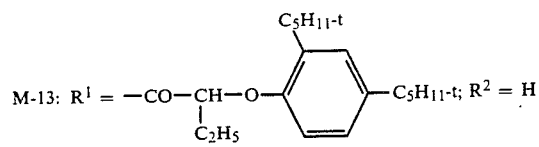
M-13: $R^1 = -CO-CH-O-$ ... ; $R^2 = H$
$\phantom{M-13: R^1 = }C_2H_5$
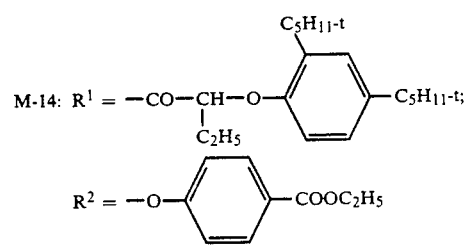
M-14: $R^1 = -CO-CH-O-$ ... ;
$\phantom{M-14: R^1 = }C_2H_5$
$R^2 = -O-$ ... $-COOC_2H_5$
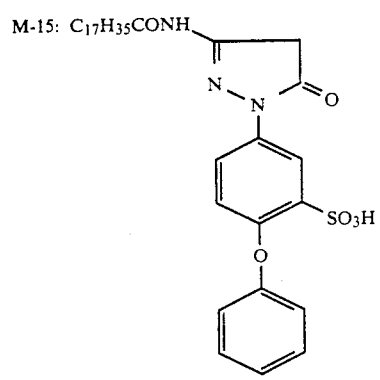
M-15: $C_{17}H_{35}CONH-$ ...
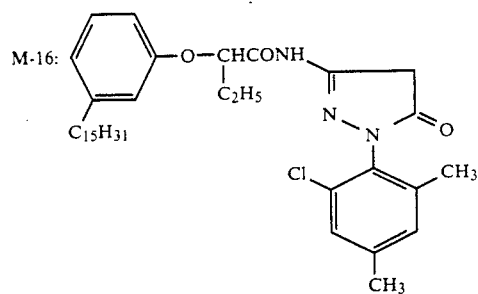
M-16:
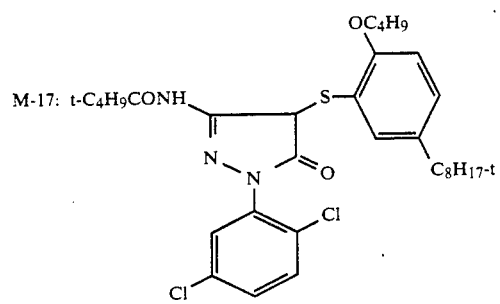
M-17: $t-C_4H_9CONH-$ ...
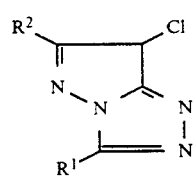

M-18: $R^1 =$ 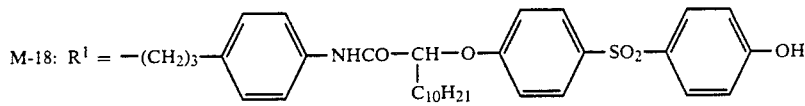

$R^2 = -CH_3$

M-19: $R^1 =$ 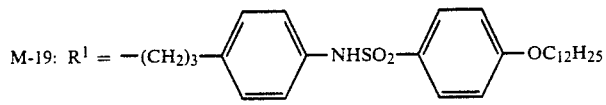

$R^2 = -CH_3$

M-20: $R^1 =$ 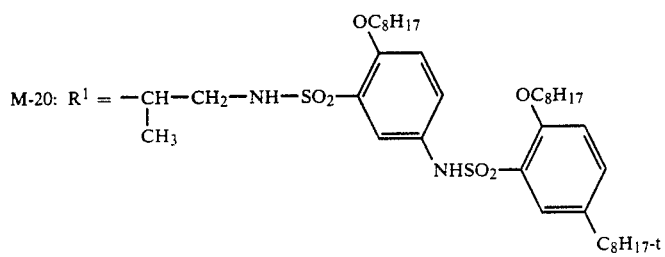

$R^2 = -C_4H_9\text{-}t$

M-21: $R^1 =$ 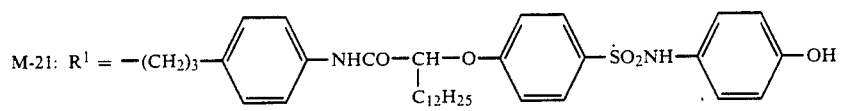

$R^2 = -CH_3$

M-22: 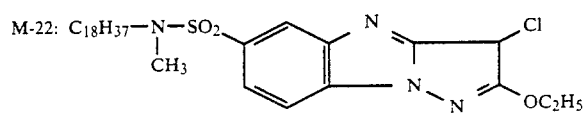

Color couplers for producing the yellow component dye image are generally couplers containing an open-chain ketomethylene group, more especially couplers of the α-acetyl acetamide type, of which suitable examples are α-benzoyl acetanilide couplers and α-pivaloyl acetanilide couplers corresponding to the following formulae:

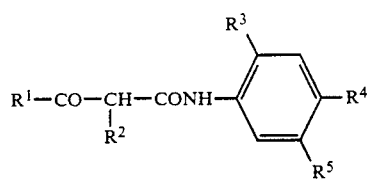

Y-1: $R^1 = -C_4H_9\text{-}t$;

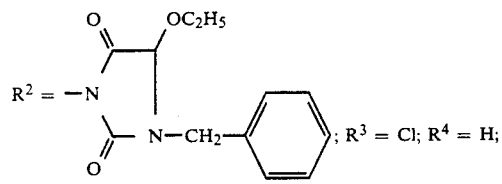; $R^3 = Cl$; $R^4 = H$;

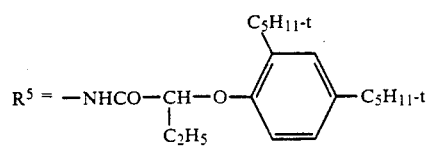

Y-2: $R^1 = -C_4H_9\text{-}t$;

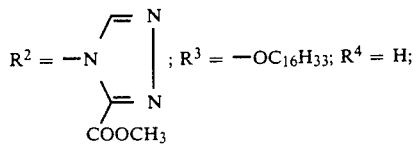
; $R^3 = -OC_{16}H_{33}$; $R^4 = H$;
$R^5 = -SO_2NHCH_3$
Y-3: $R^1 = -C_4H_9\text{-t}$;
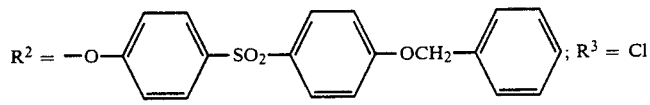; $R^3 = Cl$
$R^4 = H$; $R^5 = -NHSO_2-C_{16}H_{33}$
Y-4: $R^1 = -C_4H_9\text{-t}$;
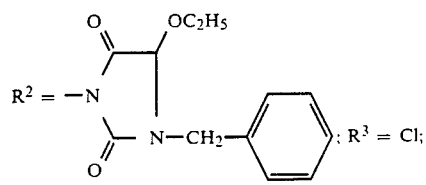; $R^3 = Cl$;
$R^4 = H$; $R^5 = -COOC_{12}H_{25}$
Y-5: $R^1 = -C_4H_9\text{-t}$;
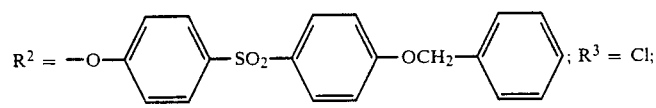; $R^3 = Cl$;
$R^4 = H$; $R^5 = $ 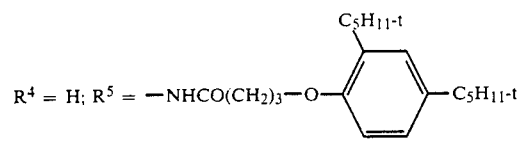
Y-6: $R^1 = -C_4H_9\text{-t}$;
$R^2 = $ 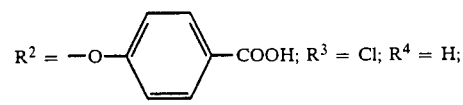; $R^3 = Cl$; $R^4 = H$;
$R^5 = $ 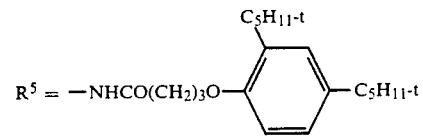
Y-7: $R^1 = -C_4H_9\text{-t}$;
$R^2 = $ 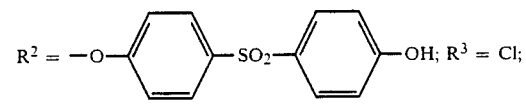; $R^3 = Cl$;
$R^4 = H$; $R^5 = -NHSO_2-C_{16}H_{33}$
Y-8: $R^1 = -C_4H_9\text{-t}$;

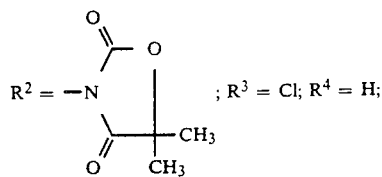; $R^3 = Cl$; $R^4 = H$;
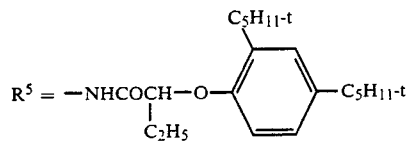
Y-9: $R^1 = -C_4H_9$-t;
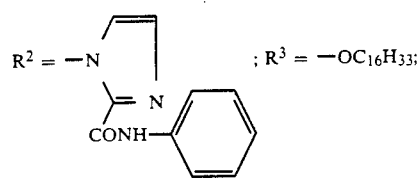; $R^3 = -OC_{16}H_{33}$;
$R^4 = H$; $R^5 = -SO_2NHCOC_2H_5$
Y-10: $R^1 = -C_4H_9$-t;
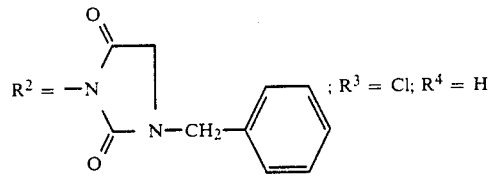; $R^3 = Cl$; $R^4 = H$
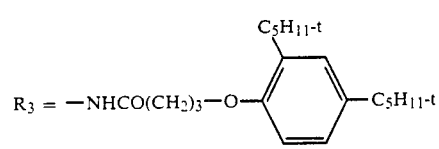
Y-11: $R^1 = -C_4H_9$-t;
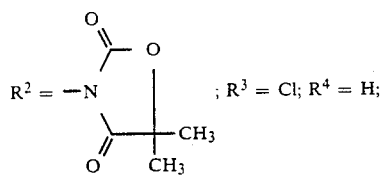; $R^3 = Cl$; $R^4 = H$;
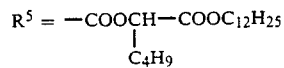
Y-12: $R^1 = -C_4H_9$-t;
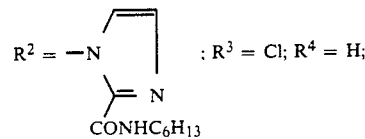; $R^3 = Cl$; $R^4 = H$;
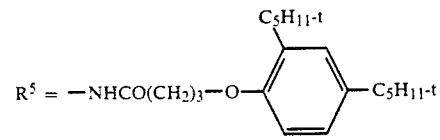
Y-13: $R^1 = -C_4H_9$-t;

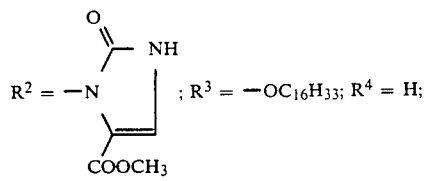
$R^5 = -SO_2NHCH_3$
Y-14: $R^1 = -C_4H_9\text{-}t$;
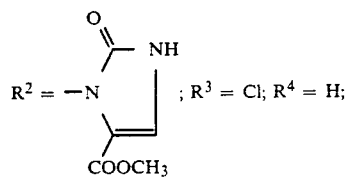
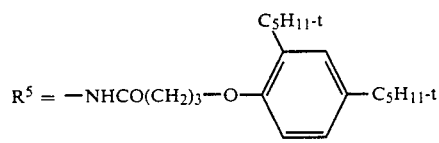
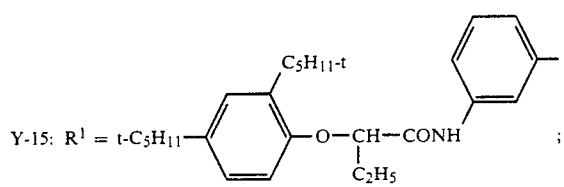
$R^2, R^4, R^5 = H; R^3 = -OCH_3$
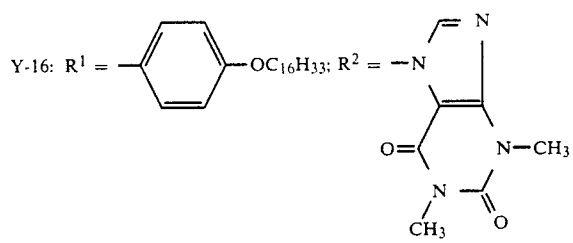
$R^3, R^5 = -OCH_3; R^4 = H$
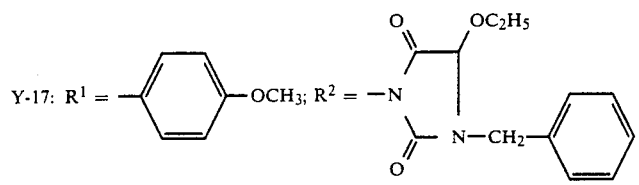
$R^3 = Cl; R^4 = H; R^5 = -COOC_{12}H_{25}$
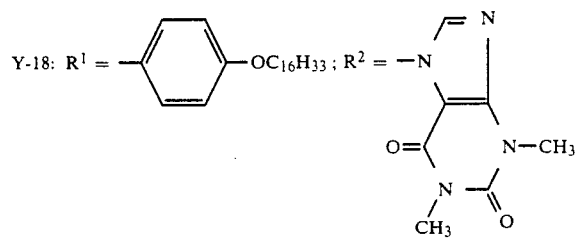
$R^3 = Cl; R^4, R^5 = -OCH_3$ Y-19: $R^1 =$ 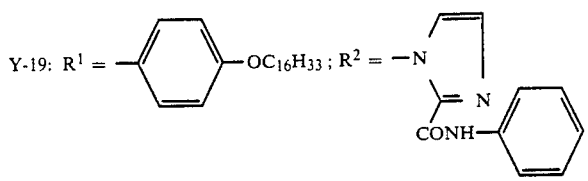

$R^3 = -OCH_3; R^4 = H; R^5 = -SO_2N(CH_3)_2$

Y-20: $R^1 = $ 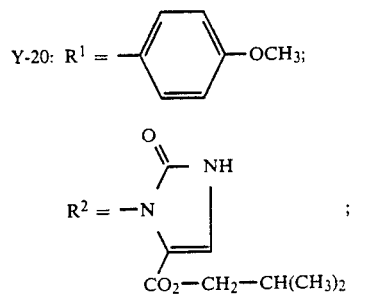

$R^3 = -OCH_3; R^4 = H;$ $R_5 = $ 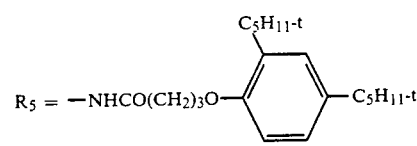

Y-21: 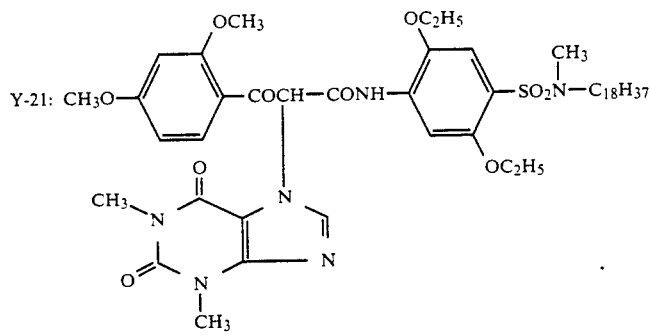

The color couplers may be 4-equivalent couplers and also 2-equivalent couplers. 2-Equivalent couplers are derived from 4-equivalent couplers in that they contain in the coupling position a substituent which is eliminated during the coupling reaction. 2-Equivalent couplers include those which are colorless and also those which have a strong color of their own that either disappears during the color coupling reaction or is replaced by the color of the image dye produced (mask couplers) and also white couplers which produce substantially colorless products on reaction with color developer oxidation products. 2-Equivalent couplers also include couplers which contain in the coupling position a releasable group which is released on reaction with color developer oxidation products and develops a certain desirable photographic activity, for example as a development inhibitor or accelerator, either directly or after one or more further groups have been released from the group initially released (cf. for example DE-A-27 03 145, DE-A-28 55 697, DE-A-31 05 026, DE-A-33 19 428). Examples of 2-equivalent couplers such as these are the known DIR couplers and also DAR and FAR couplers.

Since, in the case of DIR, DAR and FAR couplers, it is primarily the activity of the group released during the coupling reaction which is desirable, the dye-producing properties of these couplers being less important, it is also possible to use DIR, DAR and FAR couplers which produce substantially colorless products during the coupling reaction (DE-A-1 547 640).

The releasable group may also be a ballast group so that coupling products which are diffusible or which at least show weak or limited mobility are obtained during the reaction with color developer oxidation products (U.S. Pat. No. 4,420,556).

According to the invention, the color photographic recording material additionally contains at least one DIR coupler corresponding to formula I which may be arranged not only in the yellow layer, but also in the magenta layer and/or even in the cyan layer and even in a non-photosensitive layer adjacent one of the layers mentioned.

In addition to the constituents mentioned above, the color photographic recording material according to the invention may contain other additives, such as for example antioxidants, dye stabilizers and agents for influencing the mechanical and electrostatic properties. In order to reduce or avoid the adverse effect of UV light on the dye images produced with the color photographic recording material according to the invention, it is of advantage for example to use UV absorbers in one or more of the layers present in the recording material, preferably in one of the upper layers. Suitable UV absorbers are described, for example, in U.S. Pat. No. 3,253,921, in DE-C-2 036 719 and in EP-A-0 057 160.

The usual layer supports may be used for the materials according to the invention, cf. Research Disclosure No. 17 643, Chapter XVII.

Suitable protective colloids or binders for the layers of the recording material are the usual hydrophilic film formers, for example proteins, particularly gelatine. Casting aids and plasticizers may be used, cf. the compounds mentioned in Research Disclosure No. 17 643, Chapters IX, XI and XII.

The layers of the photographic material may be hardened the usual way, for example with hardeners of the epoxide type, the heterocylic ethylene imine type and the acryloyl type. It is also possible to harden the layers by the process according to DE-A-22 18 009 to obtain color photographic materials suitable for high-temperature processing. The photographic layers may also be hardened with hardeners of the diazine, triazine or 1,2-dihydroquinoline series or with hardeners of the vinyl sulfone type. Other suitable hardeners are known from DE-A-24 39 551, DE-A-22 25 230, DE-A-23 17 672 and from the above-cited Research Disclosure 17 643, Chapter XI.

Other suitable additives can be found in Research Disclosure 17 643 and in "Product Licensing Index", December, 1971, pages 107–110.

To produce color photographic images, the color photographic recording material according to the invention is developed with a color developer compound. Suitable color developer compounds are any developer compounds which are capable of reacting with color couplers in the form of their oxidation product to form azomethine dyes. Suitable color developer compounds are aromatic compounds containing at least one primary amino group of the p-phenylenediamine type, for example N,N-dialkyl-p-phenylenediamines, such as N,N-diethyl-p-phenylenediamine, 1-(N-ethyl-N-methylsulfonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine.

Other useful color developers are described, for example, in J. Amer. Chem. Soc. 73, 3100 (1951) and in G. Haist, Modern Photographic Processing, 1979, John Wiley and Sons, New York, pages 545 et seq.

After color development, the material is bleached and fixed in the usual way. Bleaching and fixing may be carried out separately or even together with one another. Suitable bleaches are any of the usual compounds, for example $Fe^{3+}$ salts and $Fe^{3+}$ complex salts, such as ferricyanides, dichromates, water-soluble cobalt complexes, etc. Particular preference is attributed to iron(III) complexes of aminopolycarboxylic acids, more especially for example ethylenediamine tetraacetic acid, N-hydroxyethyl ethylenediamine triacetic acid, alkyliminodicarboxylic acids and of corresponding phosphonic acids. Persulfates are also suitable bleaches.

EXAMPLE 1

A color photographic recording material for color negative color development was prepared (layer combination 1 A) by application of the following layers in the order indicated to a transparent layer support of cellulose triacetate. The quantities are all based on 1 m². For the silver halide applied, the corresponding quantities of $AgNO_3$ are shown. All the silver halide emulsions were stabilized with 0.4 g 4-hydroxy-6-methyl-1,3,3a,7-tetraazaindene per 100 g $AgNO_3$.

| Layer combination 1 A (comparison) | |
|---|---|
| Layer 1 | (anti-halo layer) |
| | black colloidal silver sol containing |
| | 0.2 g Ag |
| | 1.2 g gelatine |
| | 0.1 g UV absorber UV-1 |
| | 0.2 g UV absorber UV-2 |
| | 0.02 g tricresyl phosphate (TCP) |
| | 0.03 g dibutyl phthalate (DBP) |
| Layer 2 | (micrate intermediate layer) |
| | micrate silver bromide iodide emulsion (0.5 mol-% iodide; mean grain diameter 0.07 μm) of 0.25 g $AgNO_3$ containing |
| | 1.0 g gelatine |
| Layer 3 | (red-sensitized layer, medium sensitivity) |
| | red-sensitized silver bromide iodide emulsion (4.0 mol-% iodide; mean grain diameter 0.45 μm) of 5.35 g $AgNO_3$ containing |
| | 3.75 g gelatine |
| | 0.80 g cyan coupler C-14 |
| | 0.53 g cyan coupler C-17 |
| | 1.33 g TCP |
| | 0.23 g DBP |
| Layer 4 | (intermediate layer) |
| | of 1.43 g gelatine |
| | 0.74 g scavenger SC-1 |
| Layer 5 | (green-sensitized layer, medium sensitivity) |
| | green-sensitized silver bromide iodide emulsion (4.0 mol-% iodide; mean grain diameter 0.45 μm) of 3.10 g $AgNO_3$ containing |
| | 2.33 g gelatine |
| | 0.775 g magenta coupler M-12 |
| | 0.775 g TCP |
| | 0.136 g DBP |
| Layer 6 | (intermediate layer) |
| | as layer 4 |
| Layer 7 | (yellow filter layer) |
| | yellow colloidal silver sol containing |
| | 0.09 g Ag |
| | 0.34 g gelatine |
| Layer 8 | (blue-sensitive layer, medium sensitivity) |
| | blue-sensitized silver bromide iodide emulsion (4.0 mol-% iodide; mean grain diameter 0.45 μm) of 3.46 g $AgNO_3$ containing |
| | 1.73 g gelatine |
| | 1.25 g yellow coupler Y-20 |
| | 1.25 g TCP |
| | 0.152 g DBP |
| Layer 9 | (intermediate layer) |
| | as layer 4 |
| Layer 10 | (protective and hardening layer) |
| | of 0.68 g gelatine |
| | 0.73 g hardener (CAS Reg. No. 65411-60-1) |

In addition to the couplers already mentioned, the following compounds are used in Example 1:

UV absorber UV-1

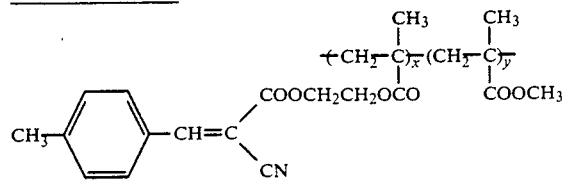

ratio by weight: x:y = 7:3

UV absorber UV-2

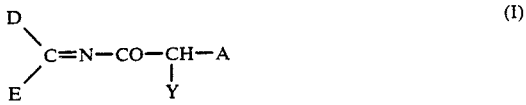

Scavenger SC-1

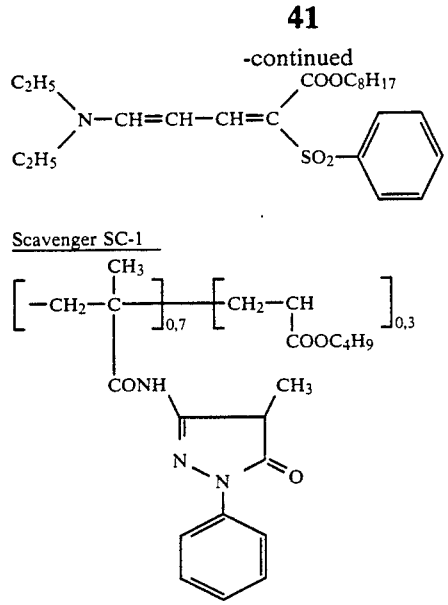

In addition, layer combination 1A contains DIR coupler DIR 1 in a quantity of 3.1 mmol/100 g AgNO₃ in each of layers 3, 5 and 8.

Other layer combinations 1B to 1L were produced in the same way, differing from layer combination 1A only in the DIR coupler used in an equivalent quantity in layers 3, 5 and 8, as shown in Table 1.

Development was carried out after exposure of a grey wedge, as described in "The British Journal of Photography", 1974, pages 597 and 598.

The results after processing are shown in Table 1. The interimage effects IIE are calculated as follows:

$$IIE_{cy} = \frac{\gamma^{red} - \gamma^w}{\gamma^w} \; ; \; IIE_{mg} = \frac{\gamma^{green} - \gamma^w}{\gamma^w}$$

where
- $\gamma_{red}$ is the gradation on selective exposure with red light
- $\gamma_{green}$ is the gradation on selective exposure with green light
- $\gamma_w$ is the gradation on exposure with white light.

The edge effect EE shown in Table 1 is the difference between the microdensity and macrodensity for a macrodensity of 0.8, as described in James, The Theory of the Photographic Process, 4th Edition, Macmillan Publishing Co., Inc. 1977, page 611. In Table 1:
- $EE_{cy}$ is the EE in the red-sensitized layer
- $EE_{mg}$ is the EE in the green-sensitized layer

TABLE 1

| Layer combination | DIR coupler | IIE$_y$ | IIE$_{mg}$ | IIE$_{cy}$ | EE$_{mg}$ | EE$_{cy}$ |
|---|---|---|---|---|---|---|
| 1 A | 1 | 48 | 122 | 84 | 0.84 | 1.08 |
| 1 B | 3 | 34 | 102 | 68 | 0.74 | 0.78 |
| 1 C | 4 | 4 | 62 | 38 | 0.41 | 0.63 |
| 1 D | 6 | 24 | 78 | 37 | 0.50 | >>0.50 |
| 1 E | 7 | 5 | 52 | 32 | 0.35 | 0.47 |
| 1 F | 8 | 25 | 95 | 54 | >>0.40 | 0.60 |
| 1 G | 9 | 30 | 106 | 53 | 0.52* | 0.56* |
| 1 H | 12 | 13 | 77 | 42 | 0.27* | 0.36* |
| 1 I | 13 | 9 | 63 | 30 | 0.38 | 0.43 |
| 1 J | 14 | 19 | 105 | 48 | >>0.50 | 0.90 |
| 1 K | 29 | 53 | 134 | 68 | 0.78* | 0.91* |
| 1 L | 30 | 14 | 103 | 46 | 0.68 | 0.70 |

*for density 0.6

Table 1 shows that excellent interimage effects and edge effects can be obtained with the DIR couplers according to the invention.

If the unexposed materials 1A to 1L are stored for 14 days at 60° C./35% relative air humidity, their sensitometric data (sensitivity, gradation, density, lowest and highest exposition to light) after exposure and processing show only a negligible change in relation to the corresponding materials stored at under ambient conditions.

We claim:

1. A color photographic recording material comprising at least one photosensitive silver halide emulsion layer and a DIR coupler associated therewith, characterized in that the coupler corresponds to formula I $$\begin{matrix} D \\ \phantom{x} \searrow \\ \phantom{xx} C=N-CO-CH-A \\ \phantom{x} \nearrow \phantom{xxxxxxxxxx} | \\ E \phantom{xxxxxxxxxxx} Y \end{matrix} \quad (I)$$

in which
A represents halogen, —OR, —SR, —CONHR, —SO₂R, —SO₂NHR,

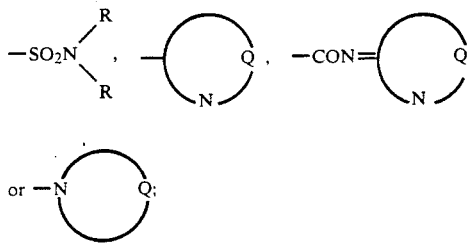

R represents alkyl, aralkyl, aryl or hetaryl;
Q represents a substituent for completing a 5- or 6-membered heterocyclic ring;
D and E, which may be the same or different, represent subtituents attached to the C atom of the C=N group by a C, O, S or N atom, including those substituents which, together with the C atom of the C=N group, complete a carbocyclic or heterocyclic ring;
Y represents a group having a silver halide development inhibiting function which is releasable during color development.

2. A recording material as claimed in claim 1, characterized in that the DIR coupler corresponds to general formula (II)

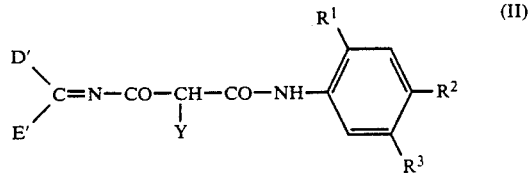

in which
D' and E' together represent a substituent for completing a heterocyclic ring to which a benzene ring may be fused;
R¹ is hydrogen, halogen, alkoxy or aroxy;
R² is hydrogen, alkoxy, alkoxycarbonyl;
R³ is hydrogen, sulfamoyl, N-alkyl sulfamoyl, N-acyl sulfamoyl, alkoxycarbonyl, acylamino;
Y is a substituent having a silver halide development inhibiting function which is releasable during the color coupling reaction.

* * * * *